US009730439B2

(12) United States Patent
Narayanan

(10) Patent No.: US 9,730,439 B2
(45) **Date of Patent: *Aug. 15, 2017**

(54) PREFORMED CONCENTRATE FOR DELIVERY OF WATER INSOLUBLE FILM FORMING POLYMERS

(75) Inventor: Kolazi S. Narayanan, Wayne, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 6 days.

This patent is subject to a terminal disclaimer.

(21) Appl. No.: 13/583,732

(22) PCT Filed: Mar. 10, 2011

(86) PCT No.: PCT/US2011/027822

§ 371 (c)(1), (2), (4) Date: Oct. 18, 2012

(87) PCT Pub. No.: WO2011/112768

PCT Pub. Date: Sep. 15, 2011

(65) Prior Publication Data

US 2013/0065759 A1 Mar. 14, 2013

(51) Int. Cl.

| | |
|---|---|
| ***A01N 25/00*** | (2006.01) |
| ***A61K 8/42*** | (2006.01) |
| ***A61K 9/66*** | (2006.01) |
| ***A01N 25/10*** | (2006.01) |
| ***C08K 5/17*** | (2006.01) |
| ***A01N 25/04*** | (2006.01) |
| ***A01N 25/02*** | (2006.01) |
| ***C08K 5/20*** | (2006.01) |

(52) U.S. Cl.

CPC ............. *A01N 25/10* (2013.01); *A01N 25/02* (2013.01); *A01N 25/04* (2013.01); *C08K 5/17* (2013.01); *C08K 5/20* (2013.01)

(58) Field of Classification Search

None

See application file for complete search history.

(56) References Cited

U.S. PATENT DOCUMENTS

| | | | | |
|---|---|---|---|---|
| 5,206,225 A * | 4/1993 | Horstmann | A01N 25/02 514/383 |
| 5,354,726 A | 10/1994 | Narayanan et al. | |
| 5,425,955 A | 6/1995 | Narayanan | |
| 6,319,949 B1 | 11/2001 | Schussler et al. | |
| 2013/0196853 A1* | 8/2013 | Narayanan | A01N 25/02 504/358 |

* cited by examiner

*Primary Examiner* — Abigail Fisher

(74) *Attorney, Agent, or Firm* — Thompson Hine LLP; William J. Davis

(57) ABSTRACT

A preformed concentrate, capable of forming emulsion/micro-emulsion upon dilution with water, for providing peripheral desiccating effect on leaves/crops comprising: (i) a water insoluble film forming polymer; (ii) a long chain substituted amide; and (iii) an oil soluble surfactant.

14 Claims, No Drawings

PREFORMED CONCENTRATE FOR DELIVERY OF WATER INSOLUBLE FILM FORMING POLYMERS

BACKGROUND OF THE INVENTION

The art has described preformed concentrates for application on leaves/crops. See Narayanan U.S. Pat. No. 5,425,955—issued Jun. 20, 1995 "Compositions Of Insoluble Film-Forming Polymers And Uses Thereof"; U.S. Pat. No. 5,766,615—issued Jun. 16, 1998 "Compositions Of Insoluble Film-Forming Polymers And Uses Thereof"; Narayanan U.S. Pat. No. 5,283,229—issued Feb. 1, 1994 "Delivery System for Agricultural Chemicals".

TECHNICAL FIELD OF THE INVENTION

The present invention relates to a preformed concentrate, capable of forming emulsion/micro-emulsion upon dilution with water, for providing peripheral desiccating effect on leaves/crops comprising: (i) a water insoluble film forming polymer; (ii) a long chain substituted amide; and (ii) an oil soluble surfactant. The peripheral desiccating effect produced by the composition of the present invention typically results in water repellency and/or delaying of the onset of fungi growth on leaves/crops.

The preformed concentrate further comprising co-solvents having a fractional dispersive solubility parameter of greater than about 50%, preferably greater than about 70% and a molar volume of greater than about 150 cc/mole. The concentrate on dilution with water or solution of agricultural active forms an emulsion/micro-emulsion or fine dispersion, which can be sprayed on leaves/crops.

The agricultural actives contemplated for use herein include bioactive, agricultural fertilizers, nutrients, plant growth accelerants, herbicides, plant growth regulators, insecticides, bactericides, fungicides, nematocides, fumigants, light stabilizers, UV absorbers, synthetic hydrocarbons, radical scavengers, resins, natural waxes, fragrances, organic solvents and monomers for polymers, disinfectants and/or combinations thereof.

In particularly preferred embodiments, the matrix of the present invention is free of toxic and environmentally objectionable solvents/components. The present invention provides a composition that finds application in providing efficient delivery of water insoluble film forming polymers alone or in combination with agricultural actives. The present invention is suitable for film forming applications such as wood protection, plant protection, rain fastness effect, peripheral desiccation effect to prevent or delay onset of growth of fungi, providing higher crop yield and the like.

DESCRIPTION OF THE PRIOR ART

Delivery of water insoluble film formers in water is a difficult task. One of the basic problems is their extreme insolubility in water. Certain types of polymers exhibit film-forming properties and when dissolved in an organic solvent, can be applied for the purpose of providing a water-resistant coating on a substrate. Usually, the film-forming polymer in the solvent is applied to the particular substrate to be coated, and the solvent is allowed to evaporate or removed leaving a film of the polymer.

This results in the film former having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the actives/chemical itself or to its subsequent application. This toxicity may also be disadvantageous with respect to handling and also affect the environment.

Typical of such film forming polymers are copolymers of N-vinylpyrrolidone with α-olefins, styrene, esters such as vinyl acetate, acrylates, acrylic acids, amides, maleic acid, mono and diesters of maleic acids, vinyl ether co-polymers and natural waxes the like.

Various attempts have been made to provide emulsified or suspension formulations. Difficulties have been encountered with respect to providing a desirably high concentration of the hydrophobic active ingredients, particularly agricultural, herbicides, pesticides etc. Emulsions (or macroemulsions) are usually unstable. The suspended droplets will eventually agglomerate and the dispersed phase will phase separate. Emulsion droplet sizes are much larger, typically one micron or more, resulting in a cloudy or milky dispersion. The nature of an emulsion may depend on the order of mixing of the ingredients and the amount of energy put into the mixing process. The final micro emulsion state will not depend on order of mixing, and energy input only determines the time it will take to reach the equilibrium state. There have been limited efforts to develop micro-emulsions.

Thus, when such hydrophobically active chemicals are formulated into a macroemulsion (sometimes referred to herein as an emulsion), it is difficult to maintain the emulsified state. This, in turn, creates problems in maintaining a uniform formulation, particularly, when the formulation is diluted with water for application to the plants, woods or as coatings.

The development of microemulsion technology has enabled formation of improved dispersions for some materials. Microemulsions are thermodynamically stable dispersions of one liquid phase into another, stabilized by an interfacial film of surfactant. This dispersion may be either oil-in-water or water-in-oil. Microemulsions are typically clear solutions, as the droplet diameter is approximately 100 nanometers or less. The interfacial tension between the two phases is extremely low.

U.S. Pat. No. 5,425,955 discloses emulsion concentrates of water-insoluble film-forming polymers which can be utilized to form water-resistant films of active ingredients, such as, agriculturally active chemicals. Methods for preparation and use of the emulsion concentrates are disclosed.

Similarly, U.S. Pat. No. 5,766,615 discloses compositions that are composed of the water-insoluble polymers, a surfactant, and a long chain alkylpyrrolidone and which form clear stable microemulsions or solutions of the insoluble polymer are obtained on the addition of water.

Most of the prior art suggests the use of alkyl pyrrolidone solvent as one of the major components of the matrix. However, in recent years more stress has been on environmentally safe or EPA approved chemicals that can be safely applied to agricultural fields on growing crops. The compositions of the present invention can be comprised of all components approved by EPA for application on growing crops or those exempt from approval.

U.S. Pat. No. 5,283,229 discloses the combination of alkyl pyrrolidones and dialkyl amides. The invention particularly relates to a concentrate which is composed of an agriculturally active chemical, a surfactant, and a solvent composed of first and second components. The first component is selected from the group consisting of N-methylpyrrolidone, ethylene carbonate, propylene carbonate, butylene carbonate, N—N,dimethylimidazolone, dimethyl formamide, dimethylacetamide, dimethylsulfoxide, and mixtures thereof and the second component is selected from the group consisting of octylpyrrolidone, dodecylpyrrolidone, N-2-ethylhexylpyrrolidone, and mixtures thereof.

U.S. Pat. No. 5,317,042 disclosed a clear stable, efficacious aqueous microemulsion of a pyrethroid insecticide, alone, or in a complex mixture, obtained by mixing the insecticide with an inert matrix composition containing a defined mixture of nonionic surfactant to form a microemulsion concentrate, and diluting with water. The inert matrix composition consisted of a predetermined mixture of nonionic surfactants which also included nonylphenol ethoxylate with HLB>6. However, the presence of nonylphenol ethoxylate in the formulation may be considered detrimental in some cases.

However, the microemulsion concentrates of the above related patents require a large amount of N-alkyl pyrrolidones including N-methylpyrrolidone for increased loading of the active ingredients. N-methylpyrrolidone is listed under California Proposition 65 with certain labeling restrictions. Furthermore, the use of the hydrophobic solvents disclosed in U.S. Pat. Nos. 6,541,516 and 6,187,715 limits the type of active ingredients and the loading depending on the solubility of the active ingredients in the hydrophobic solvent chosen.

Thus it is always desired to look for the options which are environmentally safe and approved and are compatible with the actives of interest. Thus, a need exists for alternative methods of dispensing of hydrophobic actives and/or water insoluble film forming polymers, which are particularly used in agricultural fields.

Accordingly, it is an object of this invention to provide a preformulate concentrate which provides stable emulsion/micro emulsion upon dilution with water, and which can be used within a relatively long time, without significant hydrolysis or precipitation.

Accordingly it is one of the objectives of present invention to provide substantially stable homogeneous, water soluble or water emulsifiable, preformed concentrate which is suitable for providing delivery system for film formers particularly, water insoluble film polymers alone or in combination with agricultural actives.

This invention provides a new class of preformed concentrates which provides a peripheral desiccating effect on leaves and crops, which not only causes water repellent surfaces but also delays the onset of fungi growth. The preformed concentrate of the present invention can be used alone or mixed with agricultural active, on dilution with at least 10 fold water to form an emulsion/micro-emulsion which can be sprayed on to the crops.

Thus it is one of the objectives of the present invention to provide a preformed concentrate, capable of forming emulsion/micro-emulsion upon dilution with water, for providing peripheral desiccating effect on leaves/crops comprising:

(i) a water insoluble film forming polymer;
(ii) a long chain substituted amide;
(iii) an oil soluble surfactant; and optionally co-solvents.

The preformed concentrate of the present invention can be used as a coating for substrates, such as wood, metal, glass and the like; used as an adjuvant to enhance crop protection and yield and is compatible with several crop protection concentrates especially on dilution in water at use level; provides a water resistant film on application to surfaces, especially growing crops; provides rain-fastness during the crop growth; provides effective enhancement in the crop protection against the pathogen or pests like fungicides and insecticides and herbicides; provides increased yield of the crop; and is capable of being used as a granulating fluid to produce water-dispersible granules with the adjuvant incorporated.

SUMMARY OF THE INVENTION

I have discovered a new class of preformed concentrates of water-insoluble film-forming polymers which provides a peripheral desiccating effect on leaves and crops, which not only causes water repellent surface on them but also delays the onset of fungi growth.

In accordance with the present invention, there is provided a preformed concentrate, capable of forming emulsion/micro-emulsion upon dilution with water, for providing peripheral desiccating effect on leaves/crops comprising:

(i) a water insoluble film forming polymer;
(ii) a long chain substituted amide; and
(iii) an oil soluble surfactant.

The water-insoluble polymers used in the present invention are selected from the group consisting of water-insoluble graft polymer of N-vinylpyrrolidone and an α olefin selected from the group consisting of $C_{16}$ α-olefins in a 50:50 weight ratio and $C_{20}$ α-olefins in a 20:80 weight ratio; polyacrylate; polystyrene acrylate copolymer; polystyrene butadiene copolymer; natural wax, polyisoprene copolymer and combinations thereof.

In one of the preferred embodiments, the water-insoluble polymer is graft polymer of vinylpyrrolidone and α-olefin wherein the polymerized N-vinylpyrrolidone fraction is present in more than about 5 percent on a weight basis. Preferably, the weight percent of polymerized N-vinylpyrrolidone fraction is at least about 10 percent. The α-olefin should contain from 8 to 30, and preferably, from 16 to 20 carbon atoms.

A suitable solvent, used for the present invention, to solubilize the polymer with wetting property is a long chain substituted amide, preferably a dialkyl acid amide, having the formula:

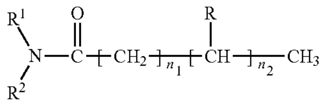

wherein, $R^1$ and $R^2$ are lower alkyl with 1-4 carbon atoms, alicyclic or aromatic; $n_1$=0-18, $n_2$=0-18 and R=H. Preferably, $R^1=R^2=CH_3$; R=H, $n_2$=0; $n_1$=5-11, and more preferably 7-9.

In a preferred embodiment, the dialkyl acid amide is selected from the group consisting of N,N-dimethyl hexamide, N,N-dimethyl octanamide, N,N-dimethyl decanamide, N,N-dimethyl dodecanamide, N—N-dimethyl decamide and N,N-dimethyl tetradecanamide.

The oil soluble surfactant includes anionic, non-ionic and mildly cationic surfactants and combinations thereof well known to those skilled in the art.

The preformed concentrate of the present invention can further comprise co-solvents having a fractional dispersive solubility parameter of greater than about 50%, preferably 70% and a molar volume of greater than about 150 cc/mole. The co-solvents can be selected from the group consisting of pyrrolidones, soybean oil, rapeseed oil, long chain alcohols, long chain ketones, long chain esters, ethers, hydrocarbons, and aromatic petroleum oils.

In a preferred embodiment, the co-solvent is a long-chain alkylpyrrolidone selected from the group consisting of octylpyrrolidone, dodecylpyrrolidone, N-2-ethylhexylpyrrolidone, and mixtures thereof.

In yet another preferred embodiment the co-solvent is aromatic petroleum oil comprising about 60% of heavy aromatic solvent naphtha and about 40% of middle distillate solvent extractant.

The amount of amide in the preformed concentrate is from about 5-80%, preferably 8-50% weight percent, the amount of water insoluble film forming polymer is from about 1 to 60 weight percent, the amount of surfactant is from about 1 to 25 weight percent and the amount of co-solvent is from about 0 to 60 weight percent based on the total weight of the preformed concentrate.

The preformed concentrate additionally may comprise co-emulsifiers, wetting combinations, ionic emulsifiers, stabilizers and surface active buffers and mixtures thereof.

Typically the inventive compositions are added to a bioactive material either individually or severally by using combinations of active ingredients and sprayed on growing crops in post emergent application or on the soil in pre-emergent application. The benefit derived by the use of the inventive composition is delayed fungi attack, reduced level of fungi infestation by using fungicides, and ultimately improved yield of crops. With other products inventive compositions can provide improved spreading, sticking, and rain-fastness of the protected target ingredient. Typical use level of the inventive composition is 0.01 to 1.0% in the spray solution, preferably 0.1-0.3%. When added in the concentrate or to form water dispersible granules, the level of addition of the inventive composition is: 1-25%, preferably 2-15%, most preferably 5-15%.

The concentrate results in stable emulsion/dispersions when diluted with 10-99.99 wt. % water containing 0.0005 to 5 wt. % of said hydrophobic actives based on the total diluted matrix composition.

Another preferred embodiment of the present invention provides a preformed concentrate comprising, by weight:

(a) 5-80% of a straight long chain substituted amide;

(b) 0-60% of naturally occurring or synthetic hydrophobic oils as diluent;

(c) 1-60% of a water insoluble graft polymer of N-vinylpyrrolidone in combination with a olefins; and (d) 1-25% of an oil soluble surfactant soluble in the matrix.

The invention further provides a method for providing peripheral desiccating effect or water repellency to delay onset of growth of fungi on leaves/crops comprising of mixing the preformed concentrate of present invention with agricultural active, diluting it with at least 10 fold water to form an emulsion/micro-emulsion followed by spraying it to the crops.

The agricultural active is selected from bioactive, agricultural fertilizers, nutrients, plant growth accelerants, herbicides, plant growth regulators, insecticides, bactericides, fungicides, nematocides, fumigants, light stabilizers, UV absorbers, synthetic hydrocarbons, radical scavengers, resins, natural waxes, fragrances, disinfectants and/or combinations.

One of the embodiments of the present invention provides the matrix composition which can be used as a coating for substrates, such as wood, metal, glass and the like. The composition can be used as an adjuvant to enhance crop protection and yield is compatible with several crop protection concentrates especially on dilution in water at use level. The composition provides a water resistant film on application to surfaces, especially growing crops; rain-fastness during the crop growth; effective enhancement in the crop protection against the pathogen or pests like fungicides and insecticides and herbicides. The composition enormously reduces the huge quantity of oil which is added to the spraying solution used for the crop protection against fungi, provides increased yield of the crop and is capable of being used as a granulating fluid to produce water-dispersible granules with the adjuvant incorporated.

DESCRIPTION OF PREFERRED EMBODIMENTS

The composition of the present invention is suitable for the delivery of film forming polymers, particularly water insoluble film polymers, with or without the combination of agricultural actives. The approach is environmentally safe and at the same time has broad area of applications in term of crop protection and increased crop yield.

While applicants do not wish to be bound by any theories, it is believed that the mechanism of enhancement of crop protection and crop yield is generally attributed to the ability of preformulate concentrate of the present invention to form an emulsion/micro-emulsifiable film over the leaves or crops which in turn produces a "peripheral desiccating effect". This peripheral desiccating effect actually keeps the surface of leaves dry by making the periphery/exterior of the leaves hydrophobic or water repellent thus preventing the onset of growth of fungi or delaying it, and hence the crops are prevented from fungal attack and produces better yield.

The straight long chain substituted amides, particularly dimethyl amides, with their wetting properties and hydrophilicity/hydrophobicity, solubilize the film forming polymers. Another important features of the long chain substituted amides useful herein is their proven environmental safety by various regulatory authorities.

The present invention relates to a preformed concentrate, capable of forming emulsion/micro-emulsion upon dilution with water, for providing peripheral desiccating effect on leaves/crops comprising:

(i) a water insoluble film forming polymer;

(ii) a long chain substituted amide; and (iii) an oil soluble surfactant.

The preformed concentrate of the present invention is uniquely formulated to provide an efficient stable emulsion/micro-emulsion/dispersion of film forming polymers which on dilution with water along with agricultural actives produces films of the particular film forming polymer on a given substrate.

As used herein, the term "micro-emulsion" means an oil-in-water or water-in-oil, transparent thermodynamically stable dispersion of two or more immiscible liquids or a solid in a liquid wherein the dispersed phase consists of small droplets with diameters in the range of about 10 to 100 millimicrons. Such micro-emulsions are clear and appear as a single phase to the naked eye.

As used herein, the term "clear" or "transparent" as applied to a liquid means that the liquid appears as a single phase without any particulate or colloidal material or a second phase being present when viewed by the naked eye.

As used herein, the term "agriculturally active or chemical or ingredient" (AAC or a.i.) means compounds and mixtures thereof which can be used as bioactive, agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, synergists, i.e., compounds which when used in conjunction with other AAC's enhance their activity and the like, as well as any other chemicals having properties which are suitable for agricultural uses in terms of application to plants or domestic uses for controlling insects and pests. The compounds are described/exemplified in detail in U.S. Pat. No. 5,283,229 (ISP), the disclosure of which is hereby incorporated by reference in its entirety.

The agricultural actives concentration should be as high as possible so long as it does not precipitate out upon dilution of the concentrate with water for a reasonable period of time and achieves the desired effect. Precipitation (crystal formation) on standing not only depletes the solution of actives; it can also lead to fouling of application equipment, i.e., sprayers, etc. With the present invention, it is possible to obtain concentrates with actives concentrations in excess of about 5 weight percent which form a stable emulsion upon being diluted with water. Preferably, the amount of active is from 5 to 30% and most preferably, 10 to 20%.

The inventive compositions can be added to the ready-to-spray solution obtained on dilution of the agricultural active concentrate (AAC) or can be incorporated to the concentrate. The concentration of the AAC can vary from 1-90%, preferably 5-60%, most preferably from 10-40%. The concentrate could be either a wettable powder, emulsifiable concentrate, microemulsion concentrate, suspension concentrate, water based emulsion, water dispersible granules, granulars, or gels or AAC coated films like cellulosic or other substrates and other formats.

The "long chain substituted amide" used for the present invention preferably can be dialkyl acid amide having the formula:

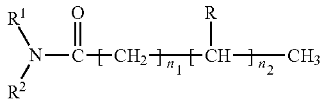

wherein, $R^1$ and $R^2$ are lower alkyl with 1-4 carbon atoms, alicyclic or aromatic; $n_1$=0-18, $n_2$=0-18, R=H. Preferably, $R^1=R^2=CH_3$; R=H, $n_2$=0; $n_1$=5-11, and more preferably 7-9.

Preferably, the amount of the amide is from about at least about 5 to 90 weight percent, more preferably from about 15 to 45 weight percent, and most preferably from about 25 to 35 weight percent. Also, mixture of these amides may be used.

In a preferred embodiment, the dialkyl acid amide is selected from the group consisting of N,N-dimethyl hexamide (N,N-Dimethyl Caproamide), N,N-dimethyl octanamide (N,N-Dimethyl Caprylamide), N,N-dimethyl decanamide (N,N-Dimethyl Capramide), N,N-dimethyl dodecanamide (N,N-Dimethyl lauramide), N—N-dimethyl decamide, and N,N-dimethyl tetradecanamide (N,N-Dimethyl Myristamide).

These compounds are sold under the trademarks Halcomide by CP Hall. See CP Hall Company, technical bulletin no. 827733 (July, 1974). See also U.S. Pat. No. 3,342,673.

The "water-insoluble film polymer" used in the present invention are selected from the group consisting of copolymers of vinyl pyrrolidone and α-olefins; polyacrylate; polystyrene acrylate copolymer; polystyrene butadiene copolymer; natural wax, polyisoprene copolymer and combinations thereof.

Polymers particularly suitable for use in the present invention include polymers, such as, Ganex 516, which is copolymer of an α-olefin and N-vinylpyrrolidone (50/50 percent mixture). Typically, such a olefins contain up to 20 carbon atoms and preferably, contain 16. The weight average molecular weight of such polymers is generally greater than about 20,000. Particularly suitable are water-insoluble polymers, such as, Agrimer AL25 (International Specialty Products (ISP) Corporation), which is a copolymer of an α olefin having the formula $C_{14}H_{29}CH{=}CH_2$ (50%) and N-vinylpyrrolidone (50%), and Agrimer AL30 (ISP Corporation), which is a copolymer of an α-olefin having 20 carbon atoms (80%), and N-vinylpyrrolidone (20%). All percents herein are percent by weight based on the total weight of the composition. See also U.S. Pat. No. 5,766,615.

Typically, the composition of the invention comprises from about 1 to 60 weight percent of the water insoluble polymer.

The term "oil soluble surfactant" used herein refers to surface active agents selected from the group consisting of ethoxylated alkyl phenols, linear aliphatic polyesters, linear aromatic polyesters, polyalkenyloxyalcohol, linear aliphatic ethoxylates, polyethoxylated castor oil, polyethoxylated carboxylates, and polyethoxylated alkylamines, tristyryl phenyl alkoxylates and acid, esters, salts. Oil soluble anionic surfactants may be used and include phosphate esters and their salts, alkyl sulfates, sulfonates, and their salts, salts of sulfate/sulfonate derived from nonylphenoxypoly(ethyleneoxy)ethanol, salts of alkylbenzene sulfonates, e.g., the sodium, calcium and alkylammonium salts, salts of alkylnaphthalene sulfonate, and sulfonated aliphatic polyesters and their salts. Also suitable are complex phosphate esters of nonionic surfactants of the ethylene oxide type which are mixtures of diesters of phosphoric acid. (See, for example, McCutcheon's, Emulsifiers and detergents (1989), published by McCutcheon's Division of M.C. Publishing Co., Glen Rock, N.J.), The oil soluble surfactant selected should preferably be soluble in the medium used.

The surfactant may be present in amounts from about 1 to 25%, preferably 5 to 22%, and most preferably, from 10 to 20%.

The inventive composition may further comprise one or more co-solvents which can be a synthetic or naturally occurring oil having a high hydrophobic character or having a fractional dispersive solubility parameter of greater than about 50%, preferably 70% and a molar volume of greater than about 150 cc/mole. These properties are defined in the C.R.C. Handbook referred to hereinabove.

Typical co-solvents include pyrrolidones, soybean oil, rapeseed oil, long chain alcohols, long chain ketones, long chain esters, ethers and hydrocarbons, aromatic petroleum oils.

In one of the preferred embodiments the co-solvent is a long-chain alkylpyrrolidone selected from the group consisting of octylpyrrolidone, dodecylpyrrolidone, N-2-ethylhexylpyrrolidone, and mixtures thereof.

In yet another preferred embodiment, the co-solvent is aromatic petroleum oil comprising about 60% of heavy aromatic solvent naphtha and about 40% of middle distillate solvent extractant. The co-solvent can be selected from alcohols, ethers, esters, ketones, aldehydes, aliphatic, aromatic, and cyclic hydrocarbons, naturally occurring flavoring agents, vegetable oils, flavoring agents, fragrances, monomers, propylene carbonate, propylene glycol, reduced vinyl pyrrolidone dimer, gamma-butyrolactone, N,N dialkyl imidazolidone, cyclohexanone, methyl ethyl ketone, benzophenone, benzyl benzoate esters of long chain carboxylic acid with greater than 4 carbon atoms or esters with an alkyl group from the alcohol segment has more than 4 carbon atoms, alcohols having greater than six carbons, or hydrocarbon solvents for those active ingredients having high solubility and with low water solubility. Also suitable as the organic diluent are: natural oils, aromatic petroleum oils including those which are commercially available distillates from crude oils having an average boiling point greater than 200° C. Typical of such materials are those sold under the trademarks Exxon 200 or Texaco 400. Of course, such aromatics should be approved for use as a carrier for hydrophobic actives cited herein. The co-solvent may be present in amounts of from about 0 to 75% preferably 0 to 60%.

The concentrate of the present invention can further comprise solvent for the polymer, co-solvents, co-emulsifiers, wetting combinations, ionic emulsifiers, stabilizers and surface active buffers and mixtures thereof. These ingredients are known in the art.

In one of the preferred embodiments the preformed concentrate of present invention is mixed with one or more of agricultural actives, which when diluted with 10-99 wt. % water result in stable emulsion/micro-emulsion/dispersions.

The agricultural actives selected from the group consisting of bioactive, agricultural fertilizers, nutrients, plant growth accelerants, herbicides, plant growth regulators, insecticides, bactericides, fungicides, nematocides, fumigants, light stabilizers, UV absorbers, synthetic hydrocarbons, radical scavengers, resins, natural waxes, fragrances, organic solvents and monomers for polymers, disinfectants and/or combinations.

Yet another preferred embodiment of the present invention provides:

Dialkyl amide of long chain acid: 10%-20%
Exxon aro 150 ULN: 0-75%
Long chain alkyl grafi co-polymer of PVP: 10-20%
Oil solubilizer emulsifier: 5-15%
IPA: Trace (<0.2%)
Total: 100%

The inventive compositions are particularly suitable for end use applications wherein films of water-insoluble polymers are formed on substrates. The films may be formed for adhesive, protective, decorative, and lubricating purposes and to impart hydrophobicity or hydrophilicity. Since it is desirable to avoid organic solvents due to their cost and adverse toxicological and environmental properties, the use of water as a solvent for the film-making procedure is preferred. With the inventive composition, it becomes possible to place such ordinarily water-insoluble film-forming polymers in an aqueous based vehicle, i.e., solution, emulsion or dispersion-solubilizing liquid, which can be handled and utilized in the same manner as a true solution of the polymer to form a film therewith. Thus, the inventive composition in microemulsion form may be coated as is, or after further dilution with water, if desired, onto a substrate. The water is then removed as by evaporation to leave the polymer film remaining.

We have further discovered that the rainfastness of agriculturally active ingredients, and in particular, pesticides, can be substantially improved by formulating the pesticides in the inventive composition including the water insoluble film-forming polymer. Thus, many pesticides, and particularly water soluble agriculturally active chemicals, are washed off by rain after they have been applied to the plants or soil. For effective pest and weed control, it takes from a few hours to three weeks for the pesticide to penetrate (translocate) into the biological system. The present invention enables the agriculturally active ingredient to be retained under the polymer film for a sufficiently long time to allow it to be effective and avoid or reduce loss from rain wash-off.

In use, the inventive composition is diluted with water and applied to the crop, plants, or soil. Normally, this dilution is carried out at the field site. As used herein, rain resistant, rainfast or rainfastness in connection with the inventive compositions means that a film formed from the composition exhibits increased resistance to removal by water washing as compared to the same composition which does not contain the film-forming polymer under the test procedures as described hereinafter.

One of the added advantage of the present invention over the prior art is to provide a "peripheral desiccating effect" on surface of the leaves which makes the surface dry and water repellent and thus prevents the onset of fungal growth. This not only reduces the fungal attack but also increases the crop yield. Particularly, growing crops benefited by the present invention are banana, potato, tea, coffee, fruit, and cereals.

In furtherance to the above mentioned advantage, the inventive composition can also be used to replace partially or totally the oil addition used in the spray solution during the crop development along with the fungicide. The various crops protected by the composition of present invention includes banana, mango, pineapple, potato, cereals, tropical fruits, tea, coffee, etc. The type of oils referred herein include a petroleum distillate, paraffin oil, mineral oil, vegetable oils and other naturally derivatized oils.

In accordance with the present invention, emulsion concentrates may be prepared by mixing an active ingredient with preformed concentrate of the present invention comprising film polymer and a solvent for the water-insoluble polymer. Such solvents can also include co-solvents due to their high solubility for polymer and capability of emulsification with commonly used emulsifiers. These concentrates may further be diluted with water to provide stable emulsions.

In a preferred embodiment, the concentrate is free of alkyl pyrrolidone and/or nonylphenol ethoxylate.

The following examples further illustrate the invention.

EXAMPLES (COMPOSITIONS 1A THROUGH 1H)

Example 1A Through 1H

Following compositions shown in Table 1 were prepared.

Composition 1A (Comparative Example)

14.6 g of dried Agrimer AL 25 [50 wt % $C_{16}$ α olefin grafted polyvinyl pyrrolidone, ISP] was dissolved in 64.3 g Exxon aromatic 150 ULN (ultra low volume naphthalene) from Exxon Chem Co, 14.6 g N-Octyl pyrrolidone (ISP) followed by addition of 6.4 g commercial Calcium dodecyl benzene sulfonate (Ninate 60E from Stepan Co). The mixture was stirred for one hour in an orbital shaker to produce a clear solution. The composition produced stable emulsion/dispersion in water.

Alternately this composition was also prepared by using 29.2 g of commercially available 50 wt. % Agrimer AL 25 in isopropanol (IPA) in the place of dried polymer along with 14.6 g N-octyl pyrrolidone and 64.3 g Exxon Am 150 (or other higher boiling hydrophobic solvents). the IPA was separated by evaporation under atmospheric or reduced pressure, followed by addition of 6.4 g Ninate 60E to produce identical composition as above.

Composition 1B 14.6 g of dried Agrimer AL 25 (50 wt % $C_{16}$ $\alpha$ olefin drafted polyvinyl pyrrolidone, ISP) was dissolved in 64.3 g Exxon aromatic 150 ULN (ultra low volume naphthalene) from Exxon Chem Co, 14.6 g commercially available Hallcomid M 8-10 (mixture of N,N dimethyl octanamide and N,N dimethyl decanamide) from Stepan Co, followed by addition of 6.5 g commercial Calcium dodecyl benzene sulfonate (Ninate 60Efrom Stepan Co). The mixture was stirred for one hour in an orbital shaker to produce a clear solution. The composition produced stable emulsion/dispersion in water.

Alternately this composition was also prepared by using 29.2 g of commercially available 50 wt. % Agrimer AL 25 in isopropanol (IPA) in the place of dried polymer along with 14.6 g Hallcomid M 8-10 and 64.3 g Exxon Aro 150 (or other higher boiling hydrophobic solvents). The IPA was separated by evaporation under atmospheric or reduced pressure, followed by addition of 6.5 g Ninate 60E to produce the inventive composition.

Composition 1C

Composition 1B was repeated except the Exxon Aro 150 ULN was replaced with Exxon Aro 150 regular grade. The composition was homogeneous and dispersible in water.

Composition 1D

Composition 1B was repeated except the Agrimer Al 25 was replaced with Agrimer AL 30 (80 wt % $C_{20}$ alkyl grafted polyvinyl pyrrolidone co polymer from ISP). The composition was homogeneous and dispersible in water.

Composition 1E

Composition 1B was repeated except the Agrimer Al 25 was replaced with dried Agrimer VA3 (copolymer of 30 wt % vinyl pyrrolidone and 70 wt % vinyl acetate copolymer from ISP). The composition was homogeneous and dispersible in water.

Composition 1F (Comparative Example)

A solution of Agrimer AL 25 in Exxon Aro 150 ULN was prepared by dissolving 15 g dried polymer in 85 g of the solvent. A homogeneous solution was obtained. However, on dilution in water at 1/100 produced broken dispersion. These are with no emulsifier.

Composition 1G (Comparative Example)

Composition 1F was repeated except Agrimer AL 25 was replaced with Agrimer AL 30. Results were similar. These are with no emulsifier.

Composition 1H (Comparative Example)

Composition 1F was repeated except Agrimer AL 25 was replaced with Agrimer VA 3. Results were similar. These are with no emulsifier.

TABLE 1

% WEIGHT COMPOSITIONS OF SOLVENT BASED POLYMER SOLUTIONS EMULSIFIABLE IN COMMERCIAL FORMULATIONS

| Ingredients | 1A | 1B | 1C | 1D | 1E | 1F | 1G | 1H |
|---|---|---|---|---|---|---|---|---|
| N-Octyl Pyrrolidone | 14.6 | 0.0 | 0.0 | 0.0 | 0.0 | 0.0 | 0.0 | 0.0 |
| Hallcomid M 8-10 | 0.0 | 14.6 | 14.6 | 14.6 | 14.6 | 0.0 | 0.0 | 0.0 |
| Exxon Aro 150 | 0.0 | 0.0 | 64.3 | 0.0 | 0.0 | 0.0 | 0.0 | 0.0 |
| Exxon Aro 150 ULN | 64.3 | 64.3 | 0.0 | 64.3 | 64.3 | 85 | 85 | 85 |
| Agrimer AL 25 as solid | 14.6 | 14.6 | 14.6 | 0.0 | 0.0 | 15 | 0.0 | 0.0 |
| Agrimer AL 30 | 0.0 | 0.0 | 0.0 | 14.6 | 0.0 | 0.0 | 15 | 0.0 |
| Agrimer VA 3 | 0.0 | 0.0 | 0.0 | 0.0 | 14.6 | 0.0 | 0.0 | 15 |
| Ninate 60E | 6.5 | 6.5 | 6.5 | 6.5 | 6.5 | 0.0 | 0.0 | 0.0 |
| Water | 0.0 | 0.0 | 0.0 | 0.0 | 0.0 | 0.0 | 0.0 | 0.0 |
| Total | 100.0 | 100.0 | 100.0 | 100.0 | 100.0 | 100.0 | 100.0 | 100.0 |

Example 2

Particle Size of the Stable Dispersions/Emulsions:

Compositions 1A, 1B, 1C were diluted at 1/10 and 1/100 with water and the droplet/particle size distribution were measured by standard analytical procedure using a) Horiba wet method and b) using Dyamic Laser light scattering techniques. There was essentially no difference in the particle/droplet distribution. Average bimodal droplet distribution was <4 microns diameter at 50% distribution and, 200 nm at 98% distribution. Compositions 1F, 1G, and 1H on dilution produced separation. These compositions could be used along with commercial formulations containing emulsifiers which would stabilize the polymer at high dilutions.

Example 3

Following examples illustrate effective rainfastness when used with commercial formulations. Rainfast evaluation was carried out using commercial Prowl, 42% Pendimethalin formulated with commercial solvents and emulsifiers. Method used is described below:

A commercial formulation (commercial Prowl with 42 wt % Pendimethaline) was diluted to end-use concentration, at 1/100 with de-ionized water containing a theoretical amount of 0.42% Pendimethalin. This composition was used as a reference sample. This sample was designated as 3R (3 reference). An appropriate dose (0.1 g-0.5 g) was uniformly applied to a 6"×6" glass plate as a 1-3" square patch. The patch was dried in laboratory hood under ambient conditions for 48-72 hrs. Triplicate samples were used for reproducibility.

After a dry film was formed, a fine spray of water was applied to simulate 0.2-2" rain wash off. Washings were collected in a waste jar. The remaining washed patch was extracted with a suitable solvent (ethanol) quantitatively in a 100 mL volumetric flask. Additional dilution in ethanol could be done if necessary to obtain UV absorbance within scale for linear regression.

The ethanol extract with appropriate dilution was examined under a calibrated UV spectrophotometer to obtain the absorbance at the Lambda max. This value was designated as: $a_w$. An identical sample was generated using the same parameters, except no washing water was used. The absorbance was designated as $a_b$. The % retention was calculated as: $[a_w/a_b]\times100$. The Lambda max for Pendimethalin was determined to be: 239 nm. 0.3 g diluted sample was used to coat on 1-2 square inch patch on 6"×6" glass plate, and typically 1.5 g-2.5 g water was used for wash. In all examples using an aromatic oil in the formulation, samples of alcohol extract from the dried spot after washing were completely evaporated in a vacuum oven to remove any residual aromatic solvent to avoid interference therefrom in the absorbance analysis.

Following samples are prepared for rain-fast evaluation.

3R: (Pendamethyline blank/no treatment)—Reference sample as described above—1/100 diluted Prowl.

3A: One g Prowl is mixed with 0.65 g composition 1A and diluted to 100 g with deionized water 3B: One g Prowl is mixed with 0.65 g composition 1B and diluted to 100 g with deionized water 3C: One g Prowl is mixed with 0.65 g composition 1C and diluted to 100 g with de-ionized water 3D: One g Prowl is mixed with 0.65 g composition 1D and diluted to 100 g with de-ionized water 3E: One g Prowl is mixed with 0.65 g composition 1E and diluted to 100 g with de-ionized water 3F: One g Prowl is mixed with 0.65 g composition 1F and diluted to 100 g with de-ionized water 3G: One g Prowl is mixed with 0.65 g composition 1G and diluted to 100 g with de-ionized water

Example 4

Compatibility of inventive compositions 1B and 1C and comparative composition 1A and mixtures of 1A and 1B, and 1C and host of commercial formulations, were evaluated by using the following procedure:

Following commercial concentrates at ready-to-use dilutions were used along with the inventive compositions at different rates and the mixed compositions were tested for any visible separation over a period of time. These compositions were sprayed on baggable fruits and any visible toxicity to fruits on applications were examined.

Concentrates Adjusted to Spray Per Hectare:

Baycor: 0.5 L in 30 L; Folicur: 0.23 L in 30 L; Siganex: 0.5 L in 30 L; Impulse: 0.64 L in 30 L; and Twist: 0.6 L in 30 L: all of the above were treated with 75 mL inventive compositions prior to dilution to 30 L to prepare the spray solutions and to use for compatibility evaluation.

Following additional commercial concentrates were also used:

Mazncozeb 80% WP: 1.5 pound was mixed in 20 pound water and further diluted to 20 gallon to produce the sprayable solution per hectare.

Bravo 40% SC: one gallon diluted to 20 gallon to produce the sprayable solution per hectare.

The above two were treated with the inventive compositions at 180 ml prior to dilution to 20 gallon to prepare the spray solution and used for compatibility evaluation. Table 2 shows the compositions and results of compatibility.

TABLE 2

COMPOSITIONS USED FOR TESTING COMPATIBILITY OF INVENTIVE COMPOSITIONS WITH COMMERCIAL PRODUCTS

| Commercial Concentrates | Dilutions | Spray rate | Additive in 30 L spray solution used in one Ha 4A | 4B | 4C | 4D | 4E | 4F |
|---|---|---|---|---|---|---|---|---|
| Currently used | Recommended use rate: 30 L | Spray solution | 1A | 1B | 1C | 1A + 1B 0.9:0.1 | 1A + 1B 1:1 | 1A + 1B 0.1:0.9 |
| Baycor | 1/60 | 30 L/Ha | 75 mL | 75 mL | 75 mL | 75 mL | 75 mL | 75 mL |
| Twist | 1/50 | 30 L/Ha | 75 mL | 75 mL | 75 mL | 75 mL | 75 mL | 75 mL |
| Folicur | 1/130 | 30 L/Ha | 75 mL | 75 mL | 75 mL | 75 mL | 75 mL | 75 mL |
| Impulse | 1/47 | 30 L/Ha | 75 mL | 75 mL | 75 mL | 75 mL | 75 mL | 75 mL |
| Siganex | 1/60 | 30 L/Ha | 75 mL | 75 mL | 75 mL | 75 mL | 75 mL | 75 mL |
| Mancozeb 80% WP | 1.5/20 | 20 gallon/Ha 75 L/Ha | 180 mL | 180 mL | 180 mL | 180 mL | 180 mL | 180 mL |
| Bravo 40% SC | 1/20 | 20 gallon/Ha 75 L/Ha | 180 mL | 180 mL | 180 mL | 180 mL | 180 mL | 180 mL |

3H: One g Prowl is mixed with 0.65 g composition 111 and diluted to 100 g with de-ionized water 3A~3B~3C~>3D>3E>3F~3G>3H>3R show the relative extent of wash off resistance.

Compatibility:

The inventive composition 3B (diluted at 1/100 containing~0.42% Pendimethalin) was stored in a tall Nessler tube and any separation was observed, compared to reference sample 3R. After storage at Zero time, 8 hr, 24 h, and 48 hrs, 1 g sample was withdrawn from the middle of the tube and weighed accurately and transferred into a standardized volumetric flask and quantitatively diluted to 500 ml or an appropriate dilution and absorbance at 239 nm was measured at Lambda max. The theoretical amount would be 8.4 ppm. Relative stability of the concentrate and dilutions could be assessed by examining the relative recovery data.

Results:

All compositions from 4A through 4F showed virtually no separation or no sedimentations observed from time 0 m, 10 m, 20 m, and 30 m. There was zero toxicity when sprayed on baggable fruits observed for 24 hours. The above is a standard test used in the field.

All the compositions were found to be compatible without significant separation or sedimentation.

Example 5: Compatibility of Existing Commercial Adjuvants and the Inventive Compositions Spraytex oil used at 5 L in 30 L and the inventive compositions 1A, 1B and mixtures of 1A and 1B at 1:1, 0.9:0.1, and 0.1:0.9 used at 75 mL in 30 L of spray solution.

Mixtures prepared at the ratio: 5 L Spraytex oil+Emulsifier: [30 mL-300 mL] inventive compositions and diluted to 30 L were found to be virtually free from any separation or sedimentation when observed at 5, 10, and 15 minutes. There was zero fruit toxicity when the above compositions were treated with baggable fruits.

Example 6: Film Formation and Peripheral Desiccation Effects

In a green house experiment, the inventive compositions are sprayed at the rate of: 0.05%-0.25% on growing leaves in a plantation. After air drying the leaf was treated with water and the water was found to be repelled in certain areas of the treated leaf. When challenged with a fresh charge of the fungi a delay of 1 day-7 days for fungal infestation was noticed on the treated leaves. Excellent protection from fungal attack is observed when the plant is treated with a combination of commercial fungicides along with the inventive compositions as shown in Table 2.

Example 7

The compositions shown in Table 2 are tested for biological efficacy in controlling fungi on growing crops. Compositions 4A, 4B, through 4F are tested in banana plantation, at the spray rates specified using the first five active ingredients shown in column 1 of Table 2 and compared with plots sprayed without the inventive compositions. The efficacy of the inventive additive is compared with Banole (natural oil) used at 5 L in 30 L spray solution per hectare and the inventive compositions used at 75 mL in 30 L, show much less fungi attack on the crop, and the onset of fungal infestation was delayed. Best results are obtained when inventive compositions are included in the spray solution ultimately providing better spray efficiency and improved quality and crop yield.

The Mancozeb was tested for control of fungi. Bravo was also tested for multiple crops for control of spot mildew. Treatment with the composition 1A showed improved fungi control and also higher yield of the beneficial crops. When inventive compositions are used similar results are obtained.

Example 8

Following are some additional examples of field trial results with Winter Wheat:

Example 8A

Commercially available Cyproconazole was applied at 80 g/20 L and sprayed per Acre in a growing winter wheat crops, with and without composition 1A, applied at 0.15% in the spray solution. Mildew postules reduced 81%, brown rust reduced 79%. Yield increased 3.5%. When inventive compositions are used similar results are obtained.

Example 8B

Commercially available Tebuconazole was applied at 100 g/20 L, sprayed per Acre in a growing winter wheat crops, with and without composition 1A, applied at 0.15% in the 20 L spray solution. Mildew postules reduced 31%, brown rust reduced 41%. Yield increased 1.0%, When inventive compositions are used similar results are obtained.

Example 8C

Commercially available Flutriafol was applied at 50 g/20 L, sprayed per Acre in a growing Winter Wheat crops, with and without composition 1A applied at 0.15% in the 20 L spray solution. Septoria infection reduced 27%, Mildew postules reduced 23%. When inventive compositions are used similar results are obtained.

Example 9

Following are some examples of field trial results with Potatoes:

Commercially available Flutriafol was applied at 0.3 L/Hectare in a growing Winter potatoes crop, with and without the inventive composition 1A applied at 22 mL in 14 L spray solution. Foliage blight was reduced by >50% and yield increased by 7.5%.

When inventive compositions are used similar results are obtained.

Example 10

Following are some examples of field trial results with Soybeans.

Commercially available Tebuconazole was applied at 5.3 Fl Oz/acre in a growing Soybean crop, with and without the compositions 1A applied at 0.25% in the spray solution. Leaf spotting was reduced by 42%. When inventive compositions are used similar results are obtained.

Example 11

The inventive composition also had compatibility of the mixed fungicide composition. For Example, Commercially available Dithane and Calixin when diluted with water and mixed with minimum amount of commercially available mineral oil (or spraytex oil) and commonly used emulsifier, the composition of spray solution gets separated in 10 minutes. Whereas, when the above composition was used with 0.1 l/ha of Composition 1B in 25 L total volume in water as spray solution, there was no separation for one hour. Additional additives for performance improvement (like naturally occurring or synthetic forms of minerals, clays, silica, silicates like pearlite and plant nutrients, organic and mineral fertilizers) can be used.

Example 12: Combination of Inventive Compositions and/or 1A (Table 1) with Commonly Available Mineral Oils/Spraytex Oil Inventive compositions and/or composition 1A can be blended with preoptimized amounts of the oil and additive like the emulsifiers (commonly used NP 7 to emulsify the oil). Such a blend can be used as an exclusive additive in the spray solutions.

The inventive composition 1B (in Table 1) or 1A can be blended with Spraytex oil at the ratio of: 0.1 L:3 L or 1:30 and can be used as an exclusive additive in the spray solution along with the emulsifier NP 7 or equivalent to attain the same result as above.

Thus, inventive compositions (for example 1B) or composition (1A) can be blended with Spraytex oil at a ratio: 1:5-1:200 with a preferred ratio of 1:1-1:5

Example 13

It was found that Calaxin and Dithane (commercially available formulations) mixed together at the normal dose along with reduced amount of Spraytex oil at 3 L/Ha and NP 7 in 25 L spray solution) produced better performance in Banana Crop, when used with 0.1 L of inventive composition 1B or 1A in Table 1, compared to composition where 0.1 L of composition 1A or 1B was replaced with additional amount of 4 L Spraytex oil+NP 7.

Example 14: Banana Field Trial for Assessing the Efficacy of Inventive Compositions Low and high rates of preformed concentrate of present invention were used in mixtures with different fungicides (protectant and systemic) with and without oil in the spray solutions were used for Mycosphaerellafijiensis (Black Sigatoka) disease control.

Materials and Methods

Grand Naine banana plants were used.

Each treatment was applied to a single row of 10 plants, without replicates.

Fungicide treatments are tabulated in Table 3.

TABLE 3

FUNGICIDE TREATMENTS, ACTIVE INGREDIENT AND APPLICATION RATES (L/HA) Spray Solution: 25 L/Ha.

| Treatment | Fungicide active ingredient |
|---|---|
| Bravo + Composition 1B 0.1 l | Clorothalonil 1.25 l/ha |
| Bravo + Composition 1B 0.5 l | Clorothalonil 1.25 l/ha |
| Bravo | Clorothalonil 1.25 l/ha |
| Dithane + Composition 1B 0.05 l-2 l/ha oil | Mancozeb 2.0 l/ha |
| Dithane + Composition 1B 0.5 l-2 l/ha oil | Mancozeb 2.0 l/ha |
| Dithane + Composition 1B 0.1 l-water | Mancozeb 2.0 l/ha |
| Dithane + Composition 1B 0.5 l-water | Mancozeb 2.0 l/ha |
| Dithane - 4 l/ha oil | Mancozeb 2.0 l/ha |
| Sico + Composition 1B 0.05 l-3 l/ha oil | Difenoconazole 0.4 l/ha |
| Sico- 7 l/ha oil | Difenoconazole 0.4 l/ha |
| Folicur + Composition 1B 0.05 l-3 l/ha oil | Tebuconazole 0.4 l/ha |
| Folicur- 7 l/ha oil | Tebuconazole 0.4 l/ha |
| Calixin + Composition 1B 0.5 l-3 l/ha oil | Tridemorph 0.5 l/ha |
| Calixin- 7 l/ha oil | Tridemorph 0.5 l/ha |
| Spraytex oil- 7 l/ha | Mineral oil |
| Untreated plants | |

A total of fifteen applications were done over 15 weeks in the protective fungicides, fourteen in the others.

Disease parameters Evaluated: youngest leaf infected (YLI), youngest leaf spotted (YLS), number of leaves (# Leaves) and disease severity using Stover scale modified by Gauhl.

Results and Discussion

Bravo Treatments

There was a very similar behavior between the Bravo+ Composition 1B at 0.1 L treatments and Bravo without Composition 1B. The performance was far better than untreated and Spraytex oil treatment without Bravo.

TABLE 4

INFECTION PARAMETERS OF BLACK SIGATOKA FOR BRAVO TREATMENTS, SPRAYTEX OIL AND UNTREATED PLANTS

| Treatment | YLI | YLS | # leaves | Severity |
|---|---|---|---|---|
| Bravo + Composition 1B 0.1 l | 5.8 | 7.2 | 10.5 | 0.45 |
| Bravo + Composition 1B 0.5 l | 5.7 | 7.1 | 11.1 | 0.64 |
| Bravo | 5.6 | 7.2 | 10.7 | 0.46 |
| Spraytex oil-7 l/ha | 4.6 | 5.9 | 9.9 | 1.74 |
| Untreated plants | 4.1 | 5.7 | 9.5 | 1.93 |

Dithane Treatments

Treatments with Dithane+4 L oil showed comparable results with reduced levels of oil: Dithane+2 L oil along with 0.05 L Composition 1B.

TABLE 5

INFECTION PARAMETERS OF BLACK SIGATOKA FOR DITHANE TREATMENTS, SPRAYTEX OIL AND UNTREATED PLANTS

| Treatment | YLI | YLS | # leaves | Severity |
|---|---|---|---|---|
| Dithane + Composition 1B 0.05 l-2 l/ha oil | 5.8 | 6.9 | 10.0 | 0.35 |
| Dithane + Composition 1B 0.5 l-2 l/ha oil | 5.6 | 6.8 | 10.0 | 0.43 |
| Dithane + Composition 1B 0.1 l-water | 5.9 | 7.3 | 10.5 | 0.40 |
| Dithane + Composition 1B 0.5 l-water | 6.2 | 7.6 | 10.7 | 0.35 |
| Dithane - 4 l/ha oil | 6.2 | 8.0 | 10.9 | 0.26 |
| Spraytex oil- 7 l/ha | 4.6 | 5.9 | 9.9 | 1.74 |
| Untreated plants | 4.1 | 5.7 | 9.5 | 1.93 |

Sico Treatments

Sico treatment also showed comparable results with reduced levels of oil when used with Composition 1B at 0.05 L. Sico treatment with 7 L oil and 3 L oil+Composition 1B at 0.05 L produced comparable results.

TABLE 6

INFECTION PARAMETERS OF BLACK SIGATOKA FOR SICO TREATMENTS, SPRAYTEX OIL AND UNTREATED PLANTS

| Treatment | YLI | YLS | # leaves | Severity |
|---|---|---|---|---|
| Sico + Composition 1B 0.05 l-3 l/ha oil | 5.6 | 7.8 | 10.5 | 0.63 |
| Sico- 7 l/ha oil | 5.6 | 7.4 | 10.3 | 0.67 |
| Spraytex oil- 7 l/ha | 4.6 | 5.9 | 9.9 | 1.74 |
| Untreated plants | 4.1 | 5.7 | 9.5 | 1.93 |

Folicur Treatments

Folicur with 7 L oil and Folicur with 3 L oil along with 0.05 L Composition 1B produced far better control of fungi infection compared to untreated condition and treatment with oil alone.

TABLE 7

INFECTION PARAMETERS OF BLACK SIGATOKA FOR FOLICUR TREATMENTS, SPRAYTEX OIL AND UNTREATED PLANTS

| Treatment | YLI | YLS | # leaves | Severity |
|---|---|---|---|---|
| Folicur + Composition 1B 0.05 l-3 l/ha oil | 5.2 | 6.7 | 10.3 | 1.12 |
| Folicur- 7 l/ha oil | 5.4 | 7.3 | 10.4 | 0.62 |
| Spraytex oil- 7 l/ha | 4.6 | 5.9 | 9.9 | 1.74 |
| Untreated plants | 4.1 | 5.7 | 9.5 | 1.93 |

Calixin Treatments

Calixin treatment showed better results with reduced levels of oil when used with Composition 1B at 0.05 L. Calixin treatment with 7 L oil showed higher disease pressure compared to 3 L oil+Composition 1B at 0.05 L.

TABLE 8

INFECTION PARAMETERS OF BLACK SIGATOKA FOR CALIXIN TREATMENTS, SPRAYTEX OIL AND UNTREATED PLANTS

| Treatment | YLI | YLS | # leaves | Severity |
|---|---|---|---|---|
| Calixin + Composition 1B 0.05 l-3 l/ha oil | 5.4 | 6.9 | 10.5 | 0.73 |
| Calixin + Composition 1B 0.5 l-3 l/ha oil | 5.3 | 7.3 | 9.7 | 0.84 |
| Calixin- 7 l/ha oil | 4.8 | 6.7 | 10.1 | 1.19 |
| Spraytex oil- 7 l/ha | 4.6 | 5.9 | 9.9 | 1.74 |
| Untreated plants | 4.1 | 5.7 | 9.5 | 1.93 |

CONCLUSIONS

Use of fractional (very small proportion) amount of the inventive compositions or composition of Example 1A of Table 1 could replace the use of large volumes of oil (currently used in the field) and maintain better health of the growing crop by providing improved protection from fungal infestation of the plants treated with either protective or systemic fungicides. By and large, similar trends were observed when treated with Composition 1A in the place of Composition 1B. It is recommended to validate this trend using replicated plots/rows. It is expected to have variations of results depending on the geographical locations, extent of residual fungi infestation, relative humidity, temperature, rainfall and other conditions. Additionally, lower extent of fungal growth would result in healthy plant with larger trunk diameter and growth in terms of height of the plant, higher foliar coverage, and ultimately leading to higher weight of the fruits, and quality/size of the crop yield.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

The invention claimed is:

1. A preformed concentrate, capable of forming emulsion/microemulsion upon dilution with water, for providing peripheral desiccating effect on leaves/crops consisting of: (i) a water insoluble film forming polymer; (ii) a long chain substituted amide; and (iii) an oil soluble surfactant, wherein the long chain substituted amide is dialkyl acid amide having the formula:

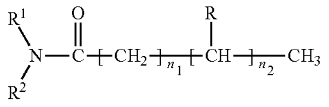

wherein, $R^1$ and $R^2$ are lower alkyl with 1-4 carbon atoms, alicyclic or aromatic; $n_1$=0-18, $n_2$=0-18, and R=H, and wherein the concentrate is free of alkyl pyrrolidone.

2. The preformed concentrate according to claim 1, wherein $R^1$=$R^2$=$CH_3$; R=H, and $n_2$=0; $n_1$=5-11.

3. The preformed concentrate according to claim 2, wherein $R^1$=$R^2$=$CH_3$; R=H, and $n_2$=0; $n_1$=7-9.

4. The preformed concentrate according to claim 1, wherein the dialkyl acid amide is selected from the group consisting of N,N-dimethyl hexamide, N,N-dimethyl octanamide, N,N-dimethyl decanamide, N,N-dimethyl dodecanamide, and N,N-dimethyl tetradecanamide.

5. The preformed concentrate according to claim 1, wherein the film-forming polymer is selected from the group consisting of water-insoluble graft polymer of N-vinylpyrrolidone and an α olefin selected from the group consisting of $C_{16}$ α-olefins in a 50:50 weight ratio and $C_{20}$ α-olefins in a 20:80 weight ratio; polyacrylate; polystyrene acrylate copolymer; polystyrene butadiene copolymer; natural wax, polyisoprene copolymer and combinations thereof.

6. The preformed concentrate according to claim 1, wherein the oil soluble surfactant includes anionic, nonionic, mildly cationic or combination thereof.

7. The preformed concentrate according to claim 6, wherein the surfactant is selected from the group consisting of tristyryl phenyl alkoxylates, alkoxylated alkyl phenols, alkoxylated linear aliphatic polyesters, linear aromatic polyesters, polyalkenyloxyalcohols, linear aliphatic alkoxylates, polyalkoxylated castor oil, polyalkoxylated carboxylates, polyalkoxylated alkylamines, phosphate esters and their salts, alkyl sulfates, sulfonates, and their salts, salts of sulfate/sulfonate derived from nonylphenoxypoly(ethyleneoxy)ethanol, sodium, calcium and alkylammonium salts of alkyl benzene sulfonates, calcium dodecylbenzene sulfonates, calcium and lithium salts of anionic alkoxylated acids, carboxylic acids, phosphoric acids and stearic acids, salts of alkylnaphthalene sulfonate, sulfonated aliphatic polyesters and their salts, complex phosphate esters of nonionic surfactants of the ethylene oxide type which are mixtures of diesters of phosphoric acid and combinations thereof.

8. The preformed concentrate according to claim 1, wherein the amount of amide is from about 5-50% weight percent, the amount of water insoluble film forming polymer is from about 1 to 60 weight percent, and the amount of surfactant is from about 1 to 25 weight percent based on the total weight of the preformed concentrate.

9. A method for providing peripheral desiccating effect or water repellency to delay onset of growth of fungi on leaves/crops comprising mixing a preformed concentrate with an agricultural active, diluting it with at least 10 fold water to form an emulsion/micro-emulsion followed by spraying the emulsion/micro-emulsion onto the leaves/crops, the preformed concentrate consisting of: (i) a water insoluble film forming polymer; (ii) a long chain substituted amide; and (iii) an oil soluble surfactant, wherein the long chain substituted amide is dialkyl acid amide having the formula:

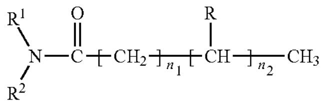

wherein, $R^1$ and $R^2$ are lower alkyl with 1-4 carbon atoms, alicyclic or aromatic; $n_1$=0-18, $n_2$=0-18, and R=H, and wherein the preformed concentrate is free of alkyl pyrrolidone.

10. The method according to claim 9, wherein the agricultural active is selected from bioactive, agricultural fertilizers, nutrients, plant growth accelerants, herbicides, plant growth regulators, insecticides, bactericides, fungicides, nematocides, fumigants, light stabilizers, UV absorbers, synthetic hydrocarbons, radical scavengers, resins, natural waxes, fragrances, disinfectants and/or combinations.

11. A method to replace partially or totally the addition of oil used in a spray solution used for the crop protection with a preformed concentrate consisting of: (i) a water insoluble film forming polymer; (ii) a long chain substituted amide; and (iii) an oil soluble surfactant, wherein the long chain substituted amide is dialkyl acid amide having the formula:

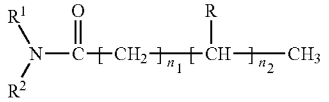

wherein, $R^1$ and $R^2$ are lower alkyl with 1-4 carbon atoms, alicyclic or aromatic; $n_1$=0-18, $n_2$=0-18, and R=H, and wherein the preformed concentrate is free of alkyl pyrrolidone.

12. The method according to claim 11, wherein the oil used in the spray solution includes petroleum distillate, paraffin oil, mineral oil, vegetable oils and other naturally derivatized oils.

13. The method according to claim 11, wherein the dialkyl acid amide is selected from the group consisting of N,N-dimethyl hexamide, N,N-dimethyl octanamide, N,N-dimethyl decanamide, N,N-dimethyl dodecanamide, N—N dimethyl decamide, and N,N-dimethyl tetradecanamide.

14. The method according to claim 11, wherein the film-forming polymer is selected from the group consisting of water-insoluble graft polymer of N-vinylpyrrolidone and an α olefin selected from the group consisting of $C_{16}$ α-olefins in a 50:50 weight ratio and $C_{20}$ α-olefins in a 20:80 weight ratio; polyacrylate; polystyrene acrylate copolymer; polystyrene butadiene copolymer; natural wax, polyisoprene copolymer and thereof.

* * * * *